(12) United States Patent
Stjernfelt et al.

(10) Patent No.: US 9,095,675 B2
(45) Date of Patent: Aug. 4, 2015

(54) FILTER

(75) Inventors: Claes Stjernfelt, Grunsund (SE); Inger Gundén, Lysekil (SE); Anders Wieselblad, Stockholm (SE)

(73) Assignee: FLODINS FILTER AKTIEBOLAG, Lysekil (SE)

( * ) Notice: Subject to any disclaimer, the term of this patent is extended or adjusted under 35 U.S.C. 154(b) by 302 days.

(21) Appl. No.: 12/864,324

(22) PCT Filed: Jan. 26, 2009

(86) PCT No.: PCT/SE2009/050076
§ 371 (c)(1),
(2), (4) Date: Aug. 26, 2010

(87) PCT Pub. No.: WO2009/093977
PCT Pub. Date: Jul. 30, 2009

(65) Prior Publication Data
US 2010/0313532 A1    Dec. 16, 2010

(30) Foreign Application Priority Data
Jan. 25, 2008 (EP) .................................... 08150680
Apr. 29, 2008 (EP) .................................... 08155349

(51) Int. Cl.
A61M 16/10       (2006.01)
B01D 46/00       (2006.01)
A61M 16/08       (2006.01)

(52) U.S. Cl.
CPC ......... *A61M 16/105* (2013.01); *A61M 16/0808* (2013.01); *A61M 16/1065* (2014.02); *B01D 46/0002* (2013.01); *B01D 46/0005* (2013.01);
(Continued)

(58) Field of Classification Search
CPC .......... B01D 46/0002; B01D 46/0005; B01D 46/0023; B01D 46/0024; A61M 16/0808; A61M 16/105; A61M 16/1055; A61M 16/1065; A61M 16/107
USPC .................... 55/482, 486, 487, 503, DIG. 35; 128/201.25, 205.12, 205.27, 205.29
See application file for complete search history.

(56) References Cited

U.S. PATENT DOCUMENTS 4,063,913 A * 12/1977 Kippel et al. .................... 96/416
4,133,656 A *  1/1979 Kippel et al. .................... 96/416
4,172,709 A   10/1979 Kippel et al.
(Continued)

FOREIGN PATENT DOCUMENTS

EP    0 265 163 A2    4/1988
EP    1 342 485 A1    9/2003
(Continued)

OTHER PUBLICATIONS

International Search Report, dated Jun. 2, 2009, from corresponding PCT application.
(Continued)

*Primary Examiner* — Robert Clemente
(74) *Attorney, Agent, or Firm* — Young & Thompson

(57) ABSTRACT

A filter to be used in the expiratory branch of a ventilator, includes a housing arranged with an inlet passage and an outlet passage, a main filter element, a pre-filter member arranged before the main filter element as seen in the flow direction and an air permeable, material capable of collecting medicament droplets in the air stream through the main filter element.

16 Claims, 4 Drawing Sheets

(52) U.S. Cl.
CPC ........ *B01D 46/0023* (2013.01); *B01D 46/0024* (2013.01); *A61M 16/1055* (2013.01)

(56) References Cited

U.S. PATENT DOCUMENTS

| | | | |
|---|---|---|---|
| 5,195,527 A | 3/1993 | Hicks | |
| 5,318,607 A * | 6/1994 | Malloy et al. | 55/323 |
| 5,590,644 A * | 1/1997 | Rosenkoetter | 128/201.13 |
| 5,783,086 A * | 7/1998 | Scanlon et al. | 210/651 |
| 5,992,413 A * | 11/1999 | Martin et al. | 128/201.13 |
| 6,105,576 A | 8/2000 | Clawson et al. | |
| 6,123,076 A | 9/2000 | Roberts et al. | |
| 6,123,752 A * | 9/2000 | Wu et al. | 96/69 |
| 6,209,541 B1 * | 4/2001 | Wallace | 128/205.27 |
| 6,702,880 B2 * | 3/2004 | Roberts et al. | 96/381 |
| 6,802,315 B2 * | 10/2004 | Gahan et al. | 128/206.12 |
| 6,926,961 B2 * | 8/2005 | Roth | 428/364 |
| 7,993,071 B2 * | 8/2011 | Clawson | 403/364 |

FOREIGN PATENT DOCUMENTS

| | | |
|---|---|---|
| JP | 63-122465 A | 5/1988 |
| WO | 00/21595 A1 | 4/2000 |
| WO | 01/02034 A2 | 1/2001 |
| WO | 2008/047108 A1 | 4/2008 |

OTHER PUBLICATIONS

Japanese Office Action, dated Feb. 12, 2013, from corresponding Japanese application.

* cited by examiner

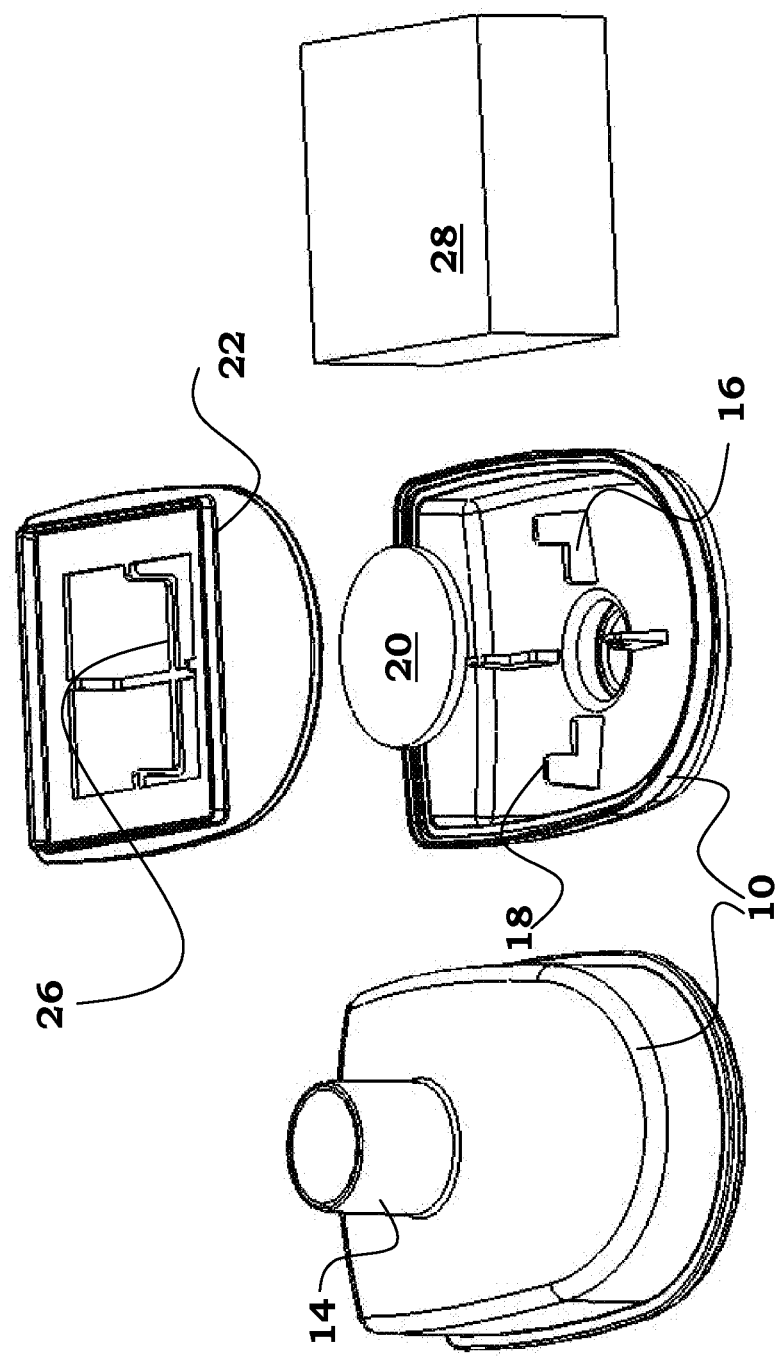

FILTER

BACKGROUND OF THE INVENTION

1. Field of the Invention

The present invention relates to a filter and in particular a filter arranged between a patient and a ventilator, capable of cleaning respiratory air.

2. Description of the Related Art

The use of ventilators in hospitals and the like treatment facilities is very common in order to aid the patient's respiration or even replace the ordinary respiration of the patient. The patient's lungs are thus connected to a ventilator via hoses forcing air into and out of the lungs. There are commonly two hoses from the ventilator, one for expiratory air and one for inspiratory air. These are usually joined in a Y-connection near the patient.

In order to provide comfort to the patient, the inspiratory air has to be pre-heated, a so called single heat system. Some ventilator systems also have heating on the expiratory limb, so-called dual heat systems.

Further, it has become more and more common to use nebulizers in connection with ventilators for administering medicament to the patient. Nebulizers are capable of aerosolizing medicament, i.e. creating very small droplets that are inspired by the patient, thereby reaching the lungs, where the medicament is further distributed into the body of the patient.

In order to prevent that the ventilator becomes contaminated by viruses and/or bacteria exhaled by the patient, a filter is arranged in the expiratory branch. Often the filter is arranged close to the ventilator, a so-called machine side filter.

The exhaled air contains quite a lot of vapour. In a single heat system this vapour will condensate in the expiratory branch, whereby water traps often are arranged in the branch. However, some vapour reaches the filter and will condense on the patient side of the filter. The condensate will wet the filter material causing the filter to function less adequately. This will cause an increase in resistance in the filter and thus a pressure drop that is negative for the patient.

In order to handle this situation, the applicant of the present patent application has developed a filter having a compartment under the filter element, in which the condensate is collected, whereby it is kept out of contact with the filter element, thereby prolonging the life of the filter.

The dual heat systems have been developed in order to reduce the amount of condensate in the expiratory branch, which condensate could be contaminated and could lead to an increased flow resistance. However, this just moves the problem with condensation. The filter element is capable of letting through the gaseous vapour comprising very tiny droplets, but when the vapour has passed the filter element, it will condense because the expiratory branch on this side of the filter is not heated. Thus, the condensate will enter the filter from this side and wet the filter element, with a reduced function as a consequence.

A further problem is the frequent use of nebulizers for administering medicament to the patient. The very small droplets should be inhaled into the lungs of the patient but a certain amount of the droplets will not be inhaled properly but will instead follow the exhaled air in the expiratory branch. A large amount of these droplets will then eventually be stuck in the filter element, severely affecting the function of the filter by clogging.

Recently a specially designed filter has been released on the market, having a wall or fixed surface facing the inlet of the filter, which surface is covered with an absorbing material. The incoming air is thus forced to deflect around the surface while the heavier medicament droplets get caught on the absorbing material. The design of this filter is however not optimal regarding keeping condensate out of contact with the filter element.

As described a few solutions have been presented to handle certain specific problems regarding filters for ventilators, but there is room for improvements regarding handling all types of problem with one filter concept.

SUMMARY OF THE INVENTION

The aim of the present invention is to remedy the above mentioned drawbacks of the state of the art technology.

Preferable embodiments of the present invention are the subject of the dependent claims.

According to a main aspect of the present invention, it is characterised by a filter to be used in the expiratory branch of a ventilator, comprising a housing arranged with an inlet passage and an outlet passage, a main filter element, and a pre-filter member arranged before the main filter element as seen in the flow direction and comprising an air permeable, material capable of collecting medicament droplets in the air stream through said main filter element.

According to another aspect of the invention, it comprises a dividing element arranged inside said housing, forming two compartments, one in communication with the inlet passage and one in communication with the outlet passage, and wherein said dividing element is arranged with a opening, in which the main filter element is placed, which compartments are capable of collecting condensate on either side of said main filter element without contact with said main filter.

According to a further aspect of the invention, said dividing element is in the form of a wall and wherein said main filter element is attached around the edges of said opening.

There are several advantages with the filter according to the present invention, where one major advantage is that it also is capable of handling medicament droplets that otherwise tend to clog the filter element. Accordingly a pre-filter member is arranged in the airflow through the device before the main filter element. The pre-filter member admits air through but catches and holds medicament droplets. The pre-filter member is of a structure that will not lead to any substantial pressure drops even if it contains a lot of medicament. This is due to the rather coarse mesh-like structure of the material, which may be polyester, polystyrene and polyurethane flexible foam.

Further, due to the design with two compartments, one on each side of the main bacteria/virus filter element condensate on both sides of the filter can be managed without the risk of the filter element becoming wet by the condensate. Thus, the filter according to the present invention is capable of being used for both single heat systems as well as dual heat systems.

The dual compartment design is preferably obtained by a divider arranged inside the filter housing and having an opening where the main filter element is attached. Thus, condensation of gaseous vapour on both sides of the filter element is handled by the divider that together with the housing forms the compartments.

In all, the filter according to the present invention handles all types of cases regarding filtering in connection with ventilators. There is thus no need for specially designed filters for a specific type of ventilator equipment and/or if nebulized medicament is administered via the respiratory branches of the ventilator.

These and other aspects of and advantages with the present invention will become apparent from the following detailed description and from the accompanying drawings.

BRIEF DESCRIPTION OF THE DRAWINGS

In the following detailed description of the invention, reference will be made to the accompanying drawings, of which FIG. 4 is an exploded view of the filter according to FIG. 3.

DETAILED DESCRIPTION OF THE INVENTION

Figure 1:
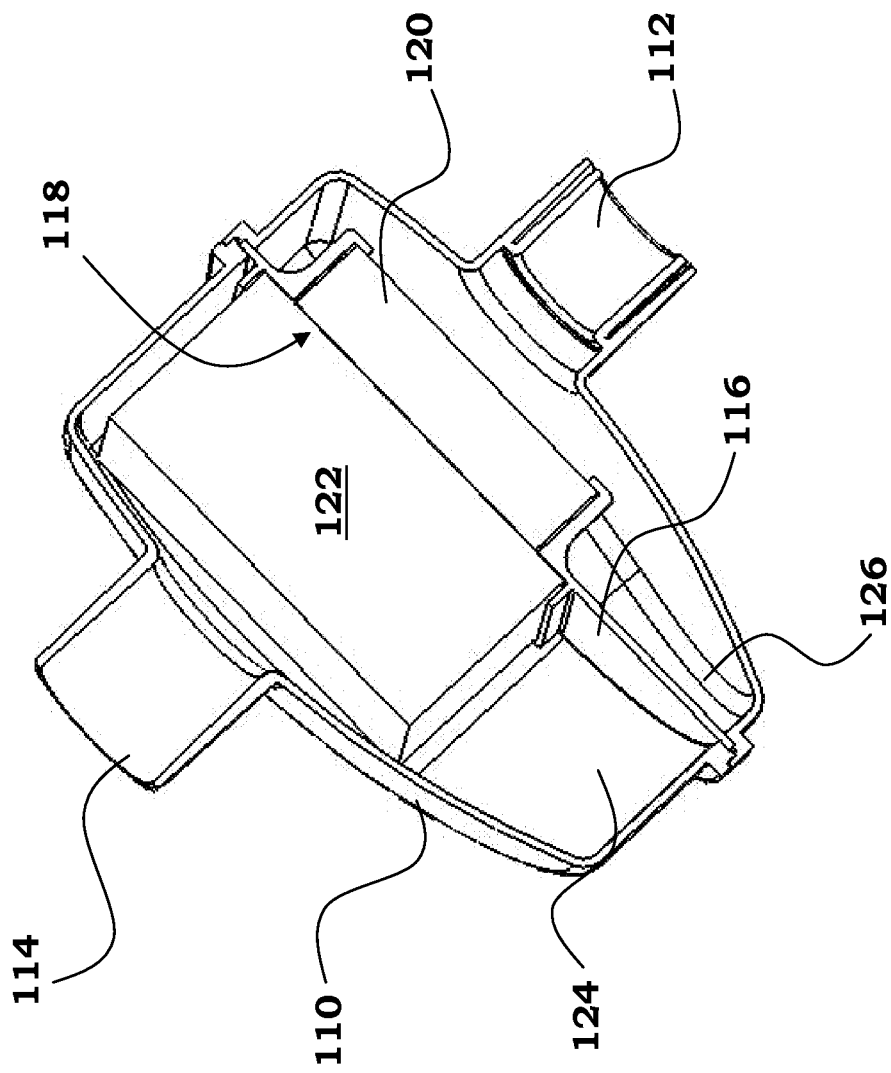
FIG. 1 is a cross-sectional view in perspective of a filter according to the present invention, FIG. 2 another embodiment of the present invention shown in FIG. 1 in cross-sectional view.

The filter shown in the figures comprises a housing 110, preferably made of plastic in two halves. The housing is arranged with an air inlet pipe connection 112 and an air outlet pipe connection 114, positioned generally opposite each other in the shown embodiment.

The filter further comprises a divider 116. The divider has a wall-like shape that preferably is attached between the two halves of the housing, thereby dividing the interior of the housing in two parts. The divider is further arranged with a central opening 118. In the opening, a pre-filter member 120 is placed, with a shape generally corresponding to the shape of the opening.

The pre-filter member is made of a suitable air permeable, material. This pre-filter member has a structure that will catch any larger droplets, like medicament droplets, while letting air through. They are often of rather coarse meshed, intertwined and/or non-woven structures providing a low pressure drop over the filter even if they have caught a lot of particles. Preferably they have a certain depth to be able of catching and holding large amounts of material. A few examples of such materials that have displayed good properties in catching medicament droplets are polyester, polystyrene and polyurethane flexible foam. There is however a number of other materials that can be used that display the same or similar properties. For instance different metals, such as stainless steel, aluminium and different alloys formed in the above mentioned structures.

Further, a main viral/bacteria filter element 122 is attached to the divider around the opening on the outlet side and thus after the pre-filter member, completely covering the passage. The housing is designed such in relation to the main filter element that there is a space between the wall of the housing and the main filter element in the area of the outlet pipe connection. The housing is further designed such that two compartments 124, 126 are formed together with the wall of the divider/holder.

The filter according to the invention is connected to a ventilator in the expiratory branch. As described above, the pre-filter member 120 will take care of any medicament droplets that are transported by the air stream, which air stream can pass through pre-filter member. However, the larger, heavier medicament drops will be caught by the filter member. Even though the per-filter member over time will contain quite a lot of medicament, the air is still capable of passing through the filter because of the structure of the pre-filter.

The air then passes through the main filter element 122, which is capable of catching bacteria and viruses, such as HEPA or ULPA filters. The main filter element could be made of any material that is capable of collecting these, such as fibre glass or PTFE, just to mention a few.

When the filter is used in a single heat system the condensate is caught in the compartment 126 on the patient side of the filter and can thus not affect the main filter element in any negative ways.

When the filter is used in a dual heat system the vapour will condense on the machine side of the filter, and in this situation the condensate is caught in the compartment 124 on the machine side of the filter. The filter is preferably designed such that the compartment on the machine side is larger than the compartment on the patient side, this being due to that excess condensate on the patient side will flow into the tube. This is not possible on the machine side due to the position of the filter, and in order to have an adequate operational life of the filter, the compartment on the machine side is made larger.

Thus, as can be appreciated, the filter according to the present invention is capable of handling different types of situations in connection with use of ventilators.

Figure 2:
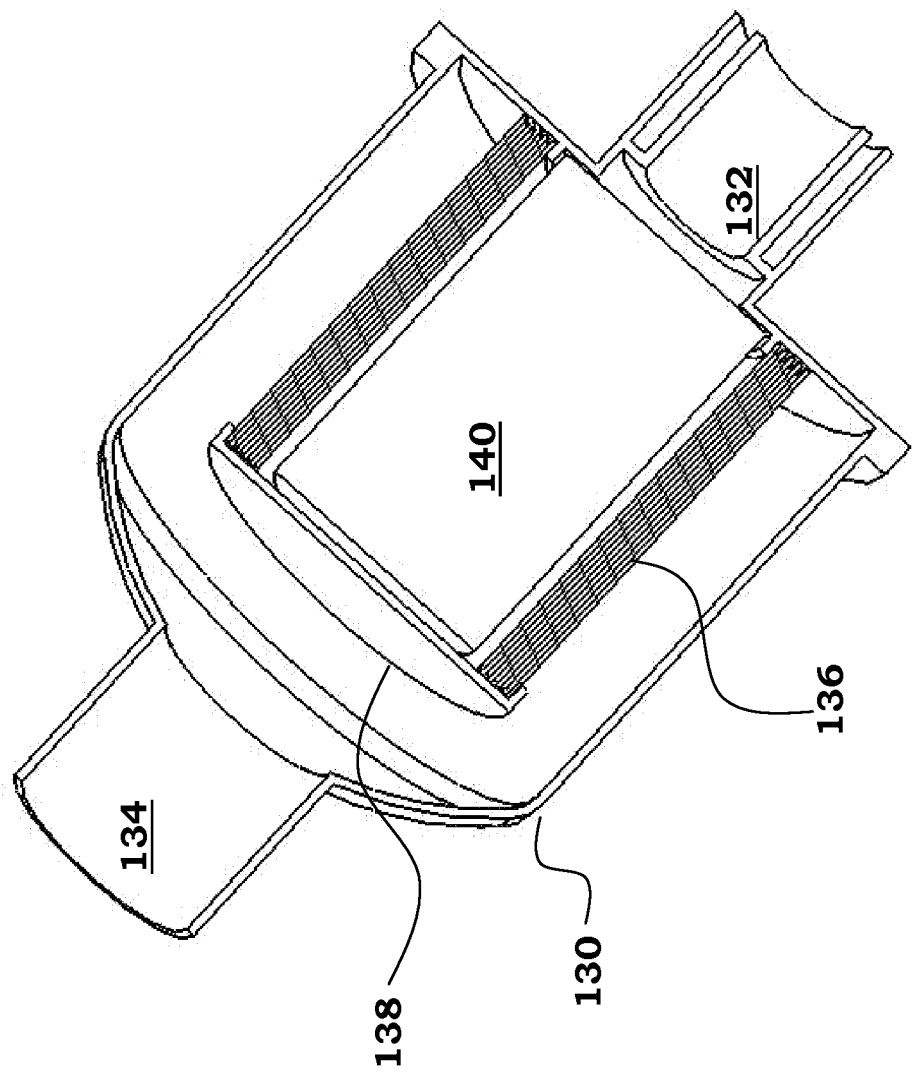

FIG. 2 displays another embodiment of the present invention. The filter housing 130 has here a more tubular or bell shape. Each end of the housing is arranged with an inlet 132 and an outlet 134 connection respectively. Inside the housing a filter 136 is arranged. The filter is in the general shape of a tube, with the walls of the "tube" consisting of pleated filter material such displaying the same properties as the main filter element of the previous embodiment. As seen, one end of the filter is arranged with a wall 138. Further, the centre of the filter is provided with a pre-filter member 140. This pre-filter member is of the same material as for the embodiment described above, thus a coarse meshed structure capable of catching the larger medicament droplets. Thus the incoming air has to pass through the pre-filter member before entering the main filter element, whereby the pre-filter member prevents medicament droplets from entering the main filter element.

Figure 3:
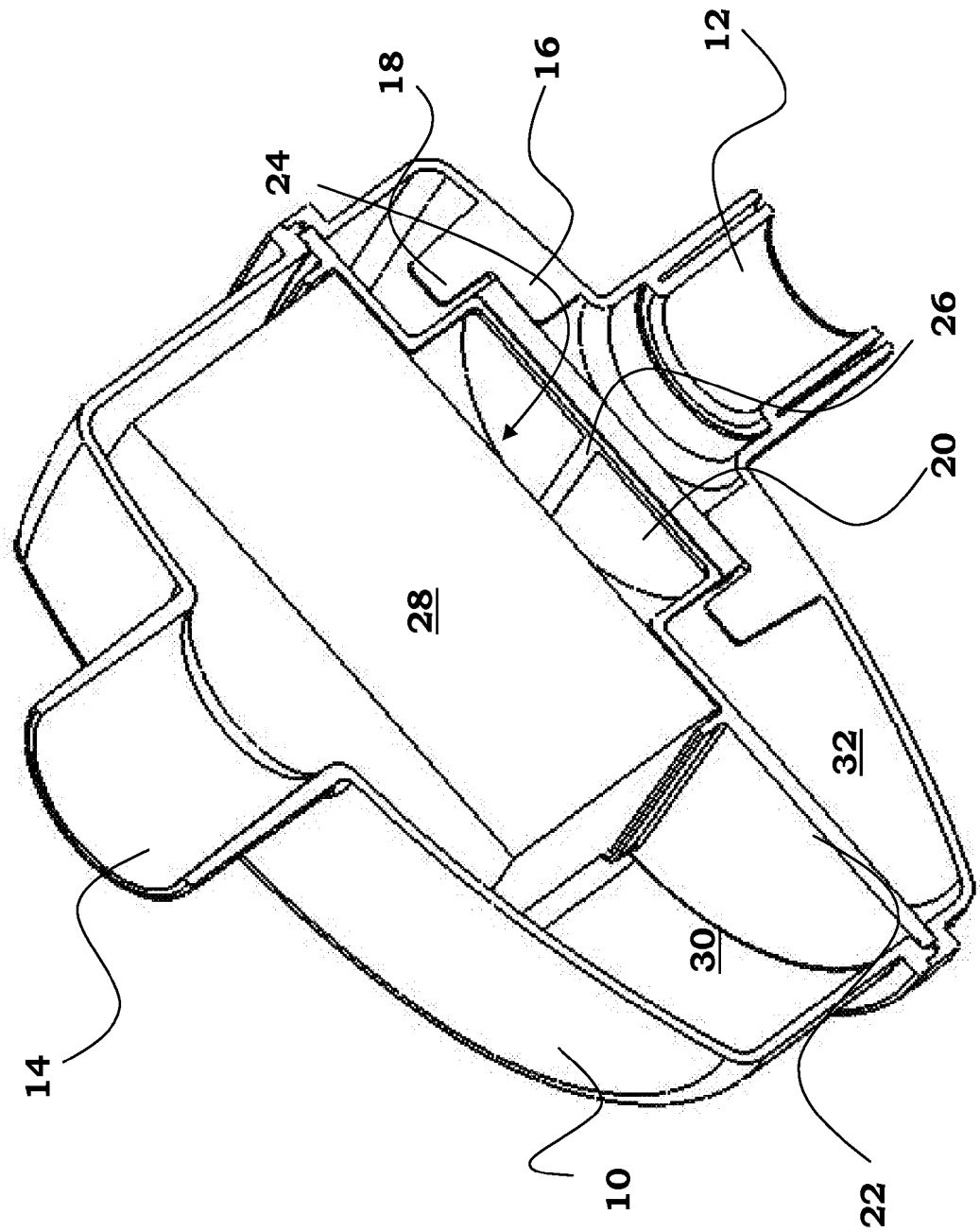
FIG. 3 is a cross-sectional view in perspective of a further embodiment of a filter according to the present invention.

FIGS. 3 and 4 show a further embodiment of the present invention. The filter shown comprises a housing 10, preferably made of plastic in two halves. The housing is arranged with an air inlet pipe connection 12 and an air outlet pipe connection 14, positioned generally opposite each other in the shown embodiment.

Around the inlet passage a number of spacer pieces 16 are attached, in the embodiment shown as four plate-like members, each arranged with a fixation part 18. On these spacer pieces a filter member 20 is placed, with a circular shape. The fixation part 18 of the spacer pieces 16 ensure that the filter member 20 is held in the proper position. The filter member is made of a suitable absorbing, yet air permeable, material. This filter member has a structure that will catch any larger droplets, like medicament droplets, while letting air through. Of course, some air will deflect around the filter member, in particular when the filter member becomes saturated with medicament because of the passage created around the filter member by the spacer pieces.

The filter further comprises a divider/holder 22. The divider/holder has a wall-like shape that preferably is attached between the two halves of the housing, thereby dividing the interior of the hosing in two parts. The divider/holder is further arranged with a central opening 24 positioned behind the filter member as seen in the direction of the air flow. In the opening, a holding structure 26 is arranged, consisting of a cross protruding towards, and in contact with, the back side of the filter member, thereby holding the filter member in the proper position.

A main viral/bacteria filter element 28 is attached to the divider around the opening on the upstream side, completely covering the passage.

The housing is designed such in relation to the main filter element that there is a space between the wall of the housing and the main filter element in the area of the outlet pipe connection. The housing is further designed such that two compartments 30, 32 are formed together with the wall of the divider/holder.

The filter according to the invention is connected to a ventilator in the expiratory branch. As described above, the filter member 20 will take care of any medicament droplets that are transported by the air stream, which air stream can pass through and/or deflect around the filter member. However, the larger, heavier medicament drops will not deflect around the filter member, but will be caught by it. Even though the filter member over time will contain quite a lot of medicament, the air is still capable of passing through the filter because of the passage created by the spacer pieces.

The air then passes through the main filter element 28, which is capable of caching bacteria and viruses, such as HEPA or ULPA filters. The main filter element could be made of any material that is capable of collecting these, such as fibre glass or PTFE, just to mention a few.

When the filter is used in a single heat system the condensate is caught in the compartment 32 on the patient side of the filter and can thus not affect the main filter element in any negative ways.

When the filter is used in a dual heat system the moist will condense on the machine side of the filter, and in this situation the condensate is caught in the compartment 30 on the machine side of the filter.

Thus, as can be appreciated, the filter according to the present invention is capable of handling different types of situations in connection with use of ventilators.

It is to be understood that the embodiment described above and shown in the drawing is to be regarded as a non-limiting example of the invention and that it can be modified in many ways within the scope of the patent claims.

The invention claimed is:

1. A filter to be used in an expiratory branch of a ventilator, comprising:
   a housing arranged with an inlet passage and an outlet passage;
   a dividing wall arranged inside said housing, dividing the interior of the housing in two compartments, one in communication with the inlet passage and one in communication with the outlet passage, which compartments are capable of collecting condensate on either side of the dividing wall;
   an opening arranged in the dividing wall;
   a main viral/bacteria filter element arranged in the compartment that is in communication with the outlet passage such that it is not contacting collected condensate, and attached to one side of the dividing wall along the edges of the opening; and
   a pre-filter member arranged in the compartment that is in communication with the inlet passage such that it is not contacting collected condensate, and placed in the opening in the dividing wall before said main filter element as seen in the flow direction, wherein the pre-filter comprises an air permeable material capable of collecting medicament droplets in the air stream through said main filter element, wherein
   said pre-filter member has a flexible foam meshed structure to provide a low pressure drop over the pre-filter.

2. The filter according to claim 1, wherein a material of said pre-filter member is foamed flexible polyester, polystyrene or polyurethane.

3. The filter according to claim 1, wherein said pre-filter member is placed in said opening of said dividing element.

4. The filter according to claim 1, wherein a material of said pre-filter member is stainless steel or aluminum.

5. The filter according to claim 1, wherein the filter is connected to a ventilator.

6. The filter according to claim 1, wherein the main filter element is capable of catching bacteria and viruses, and is a high-efficiency particulate air filter or an ultra-low penetration air filter.

7. The filter according to claim 1, wherein the main filter element is formed from fiber glass or polytetrafluoroethylene.

8. The filter according to claim 1, further comprising:
   a plurality of plate shaped spacer pieces attached around the air inlet passage, each spacer piece being arranged with a fixation part.

9. The filter according to claim 8, wherein there are four spacer pieces.

10. The filter according to claim 8, wherein each fixation part holds the pre-filter member in position.

11. A filter to be used in an expiratory branch of a ventilator, comprising:
    a tubular housing arranged with an inlet passage and an outlet passage;
    a tubular main filter element arranged in the housing, the tubular main filter element being formed from a pleated filter material; and
    a pre-filter member arranged in a center of said tubular main filter element and comprising an air permeable material capable of collecting medicament droplets in an air stream through said main filter element, wherein
    said pre-filter member displays a coarse meshed structure.

12. The filter according to claim 11, wherein a material of said pre-filter member is foamed flexible polyester, polystyrene or polyurethane.

13. The filter according to claim 11, wherein a material of said pre-filter member is stainless steel or aluminum.

14. The filter according to claim 11, wherein the filter is connected to a ventilator.

15. The filter according to claim 11, wherein the main filter element is capable of catching bacteria and viruses, and is a high-efficiency particulate air filter or an ultra-low penetration air filter.

16. The filter according to claim 11, wherein the main filter element is formed from fiber glass or polytetrafluoroethylene.

* * * * *